United States Patent [19]
Rich

[11] Patent Number: 5,165,231
[45] Date of Patent: Nov. 24, 1992

[54] ANTI-REVERSION EXHAUST SYSTEM

[76] Inventor: Donald A. Rich, 2628 O'Donnel Dr., San Pablo, Calif. 94806

[21] Appl. No.: 840,125

[22] Filed: Feb. 24, 1992

Related U.S. Application Data

[63] Continuation of Ser. No. 553,720, Jul. 16, 1990.

[51] Int. Cl.5 ............................................. F02B 35/00
[52] U.S. Cl. ....................................................... 60/316
[58] Field of Search ............................................ 60/316

[56] References Cited

U.S. PATENT DOCUMENTS 2,913,871  11/1959  Bradshaw ............................ 60/316
4,339,918  7/1982  Michikawa ........................... 60/316

FOREIGN PATENT DOCUMENTS 2558210  7/1985  France ................................. 60/316
 717880  11/1954  United Kingdom ................... 60/316

*Primary Examiner*—Douglas Hart
*Attorney, Agent, or Firm*—Thomas R. Lampe

[57] ABSTRACT

An anti-reversion exhaust system including an exhaust pipe and shroud attached to the exhaust pipe. The exhaust pipe and shroud cooperate to induce intersecting, generally opposed gaseous flows to effectively prevent reversionary flow in the direction of an associated internal combustion engine.

9 Claims, 4 Drawing Sheets

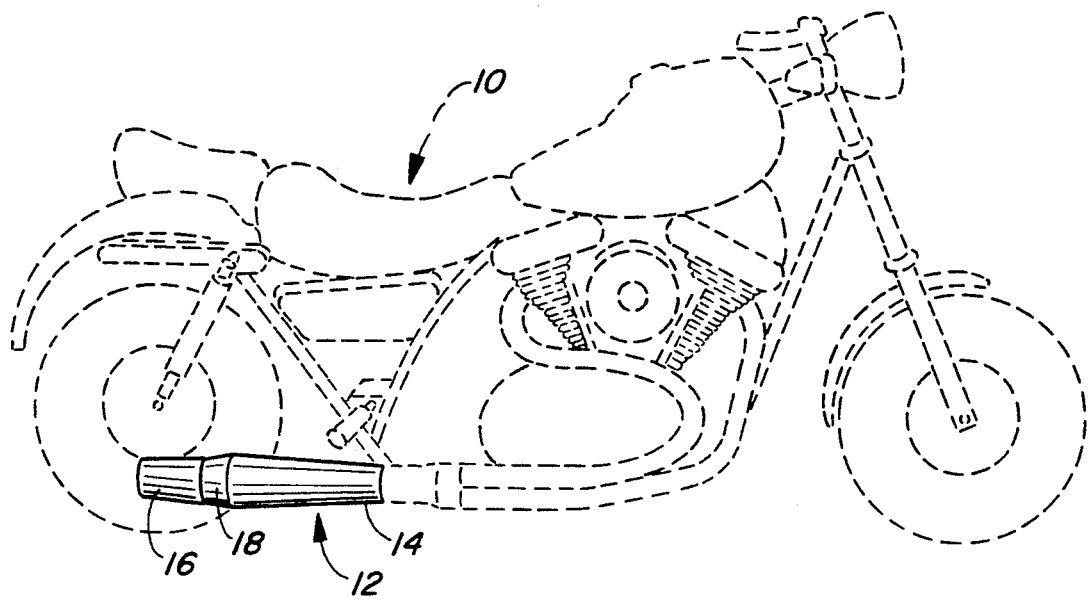
FIG._1
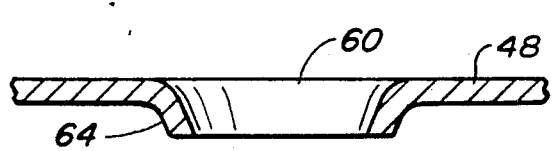
FIG._8
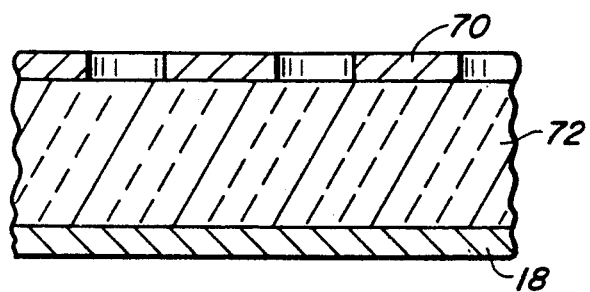
FIG._9

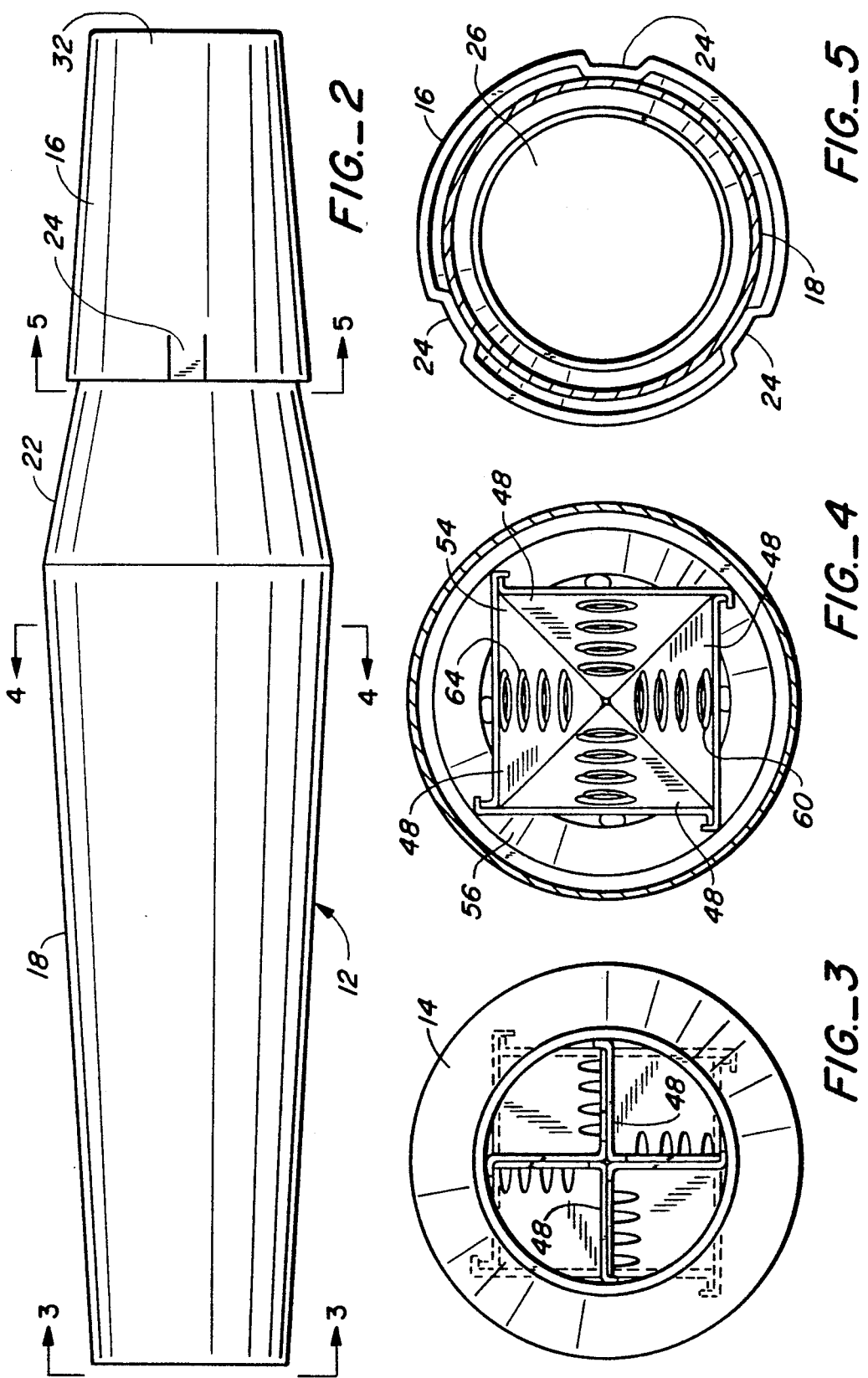

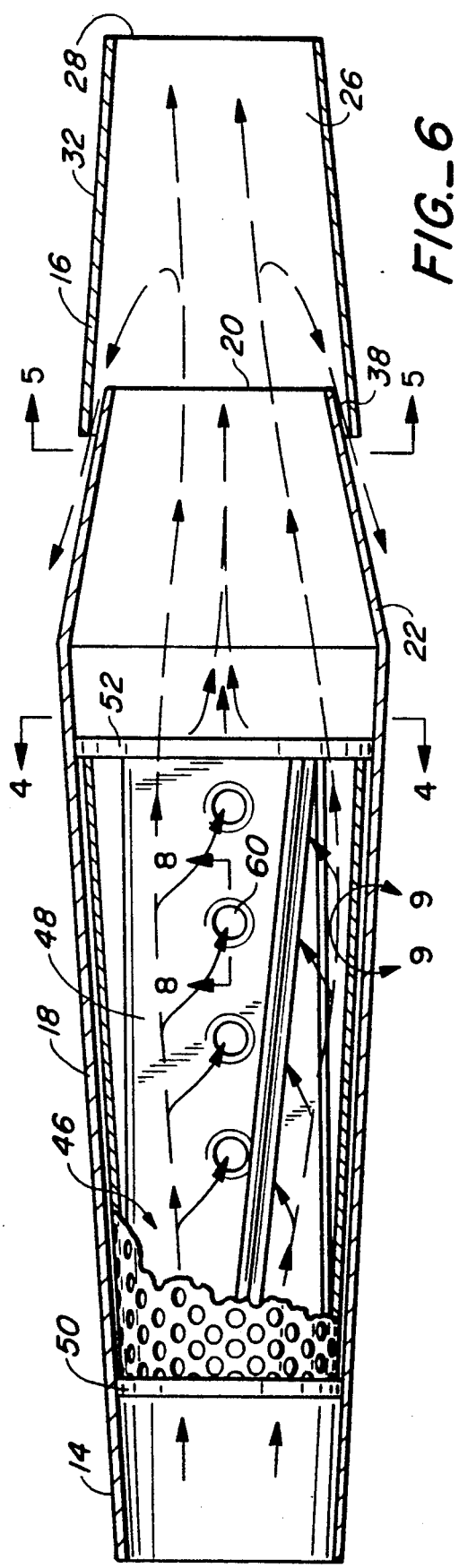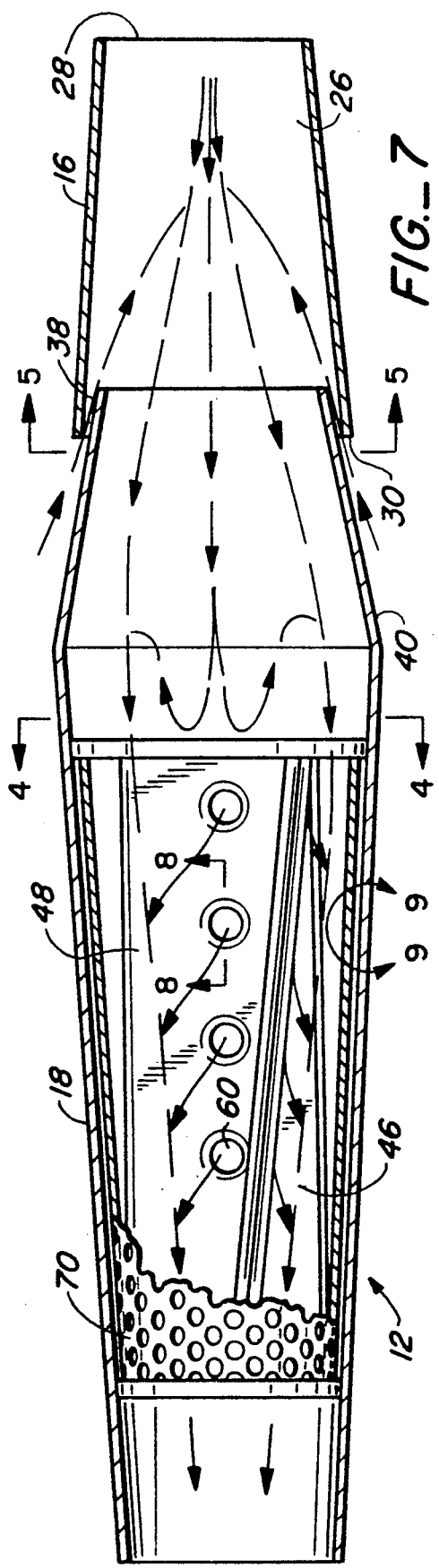

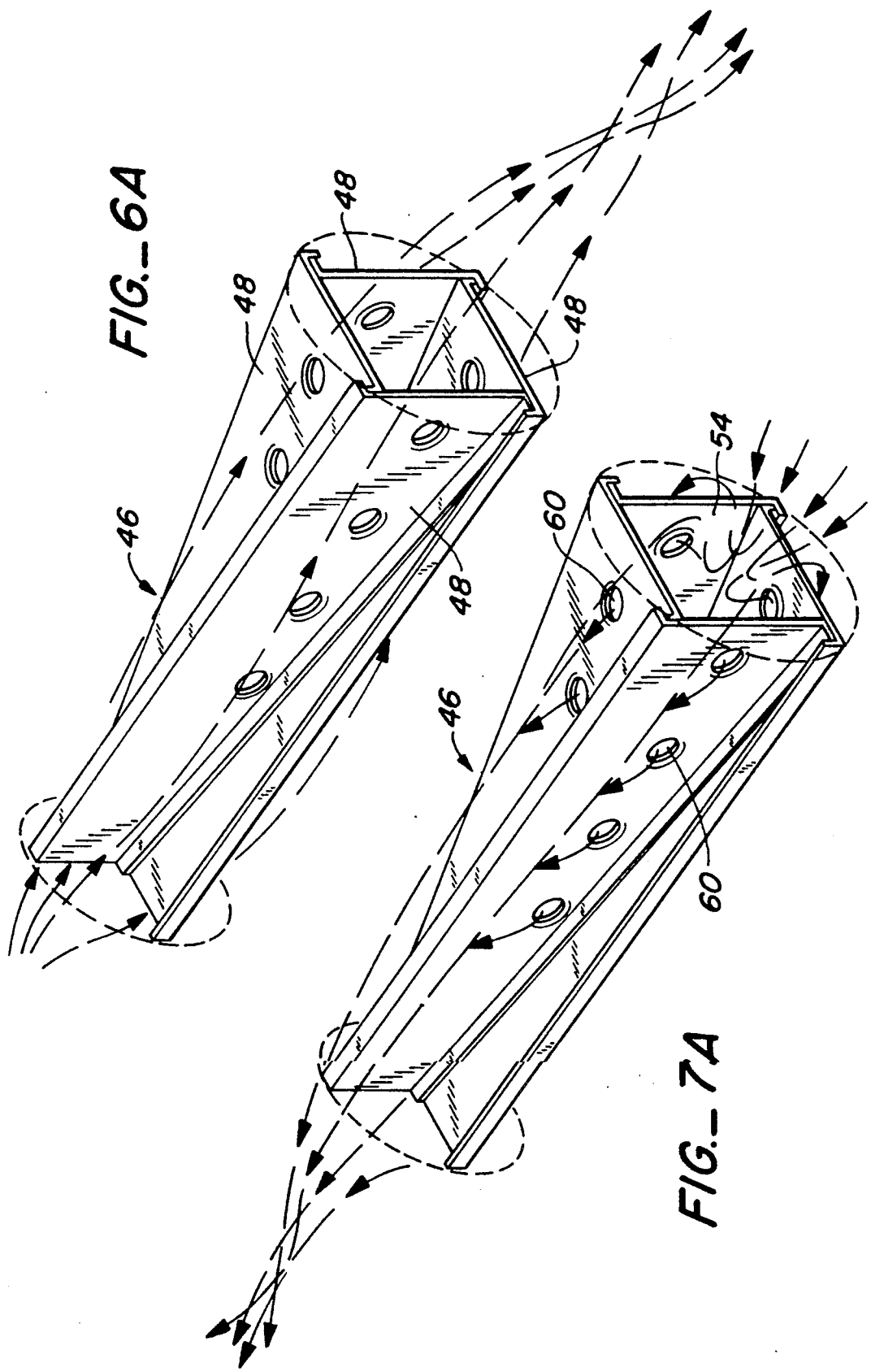

ANTI-REVERSION EXHAUST SYSTEM

This is a continuation of application Ser. No. 07/553,720 filed Jul. 16, 1990.

TECHNICAL FIELD

The present invention relates to a system for effectively preventing reversionary gases from entering an internal combustion engine. More particularly, the system includes an apparatus and method which control and direct gaseous flows within an exhaust system in a manner impeding reversional flow.

BACKGROUND ART

Internal combustion engines generate exhaust gases in a series of positive pressure pulses. Between each positive pressure pulse, negative pressure conditions are created which result in exhaust gas reversal through the exhaust system. If the back flow reaches the internal combustion engine, the performance thereof will be adversely affected. In particular, reversionary gases can enter the cylinders of the engine upon opening of the intake valves. This will result in a lowering of torque and peak horse power as well as in a fall off of the fuel economy of the engine.

A number of anti-reversionary devices have been devised for dealing with this problem. Typically, anti-reversion devices comprise baffles or barriers inserted in headers or exhaust pipes which create turbulence in the exhaust gases to impede back flow. Such devices are not effective over a full range of engine speeds. Furthermore, such devices can be relatively expensive, not only with regard to their construction but installation thereof as well.

BRIEF SUMMARY OF THE INVENTION

The system of the present invention effectively prevents reversion of exhaust gases under a full range of operating conditions. Furthermore, the apparatus of the present invention is relatively inexpensive and is readily adapted fo use with conventional exhaust systems.

The anti-reversion exhaust system of the present invention incorporates an arrangement which induces gas flow from the ambient atmosphere when a negative pressure condition is created at the end of an exhaust pipe to intersect and impede the undesirable gaseous flow entering the pipe through the exhaust port under such conditions. The preferred embodiment of the invention disclosed herein also incorporates a unique baffle means which impedes any remaining back-flow remaining after the intersection of gaseous flows takes place.

More particularly, the apparatus of the present invention includes an exhaust pipe leading from an internal combustion engine and having an end portion. The end portion defines an exhaust opening and has an outer peripheral surface leading to the exhaust opening.

A shroud is positioned adjacent to the end portion and defines a passageway leading from the exhaust opening to an exhaust port formed by the shroud.

The shroud and the outer peripheral surface of the end portion define a flow path providing communication between the ambient atmosphere and the passageway. The end portion and the shroud are co-operable upon reduction of gas pressure in the passageway caused by a negative pressure within the exhaust pipe and at the exhaust opening to induce a first gaseous flow through the flow path and into the passageway intersecting with and in general opposition to a second gaseous flow through the exhaust port resulting from the reduction of gas pressure in the passageway.

The illustrated preferred embodiment of the invention also incorporates baffle means of a specific character which impedes flow in the direction of the internal combustion engine of any portion of the second gaseous flow entering the exhaust opening after intersection thereof with the first gaseous flow.

Other features, advantages, and objects of the present invention will become apparent with reference to the following detailed description and accompanying drawings.

BRIEF DESCRIPTION OF DRAWINGS

FIG. 1 is a perspective view of a preferred embodiment of the present invention installed on a phantom-line motorcycle;

FIG. 2 is a plan view of the apparatus:

FIG. 3 is an enlarged end view of the apparatus taken along the line 3—3 in FIG. 2;

FIG. 4 is an enlarged cross-sectional view of the apparatus taken along line 4—4 in FIG. 2;

FIG. 5 is an enlarged cross-sectional view taken along the line 5—5 in FIG. 2;

FIGS. 6 and 7 are cross-sectional views of the apparatus and illustrating schematically the flow of exhaust gases during different stages of operation;

FIGS. 6A and 7A are perspective views illustrating schematically the fluid flow which occurs at the baffle means of the apparatus during different stages of operation;

FIG. 8 is an enlarged cross-sectional view taken along the line 8—8 in FIGS. 6 and 7; and FIG. 9 is an enlarged cross-sectional view taken along the line 9—9 in FIGS. 6 and 7.

DISCLOSURE OF THE INVENTION

In the embodiment of the invention disclosed herein the apparatus is employed in connection with a motorcycle 10 which is shown in phantom line in FIG. 1. It will be appreciated, however, that the invention is adapted for use with any internal combustion engine in any operational context. The apparatus itself is illustrated in FIG. 1 in a solid line format and is identified generally by reference numeral 12.

As may be seen with reference to FIG. 1 and all of the other Figures in the drawing, apparatus 12 includes an exhaust pipe 14 leading from the internal combustion engine of the motorcycle and a shroud 16 attached to the exhaust pipe.

Exhaust pipe 14 has an end portion 18, the end portion defining an exhaust opening 20 and having an outer peripheral surface 22 leading to the exhaust opening.

The shroud is positioned adjacent to end portion 18 and secured thereto by any known expedient.

In the arrangement illustrated, such securement is provided by a plurality of indents 24 formed in the shroud, in engagement with end portion 18, and attached thereto as by means of welding, fasteners, or the like.

It will be noted that the shroud 16 defines a passageway 26 leading from exhaust opening 20 to an exhaust port 28 formed by the shroud. The shroud has an inlet opening 30 larger than the exhaust port and a tapered peripheral wall 32 leading from the inlet opening to the exhaust port. End portion exhaust opening 20 is disposed within the confines of the peripheral wall 32. As may clearly be seen, the shroud has a truncated cone-like configuration and the exhaust port is smaller than exhaust opening 20.

The shroud peripheral wall 32 and the outer peripheral surface 22 of the end portion 18 define a flow path 38 providing communication between the ambient atmosphere and the passageway 26.

When exhaust gases are emitted from exhaust opening 20, a positive pressure will be created within passageway 26 of shroud 16. The pressurized gasses will exit not only exhaust port 28 but, to some degree at least, will exit flow path 38. This is the condition shown in FIG. 6 wherein gas flow is shown by the arrows.

Between the positive pressure pulses coming from exhaust opening 20, negative pressure conditions will occur within exhaust pipe 14 and within passageway 26. In conventional exhaust system arrangements a negative pressure at the exhaust opening would tend to draw exhaust gases back into the exhaust pipe and even into the internal combustion engine itself causing considerable problems as above described.

These problems are, however, obviated by the present arrangement. When a negative pressure is formed within passageway 26 of shroud 16, a first gaseous flow will be induced through flow path 38 and into the passageway. This action is perhaps best illustrated in FIG. 7 wherein arrows are utilized to schematically illustrate the first gaseous flow through the flow path 38. At the same time, of course, the negative pressure in passageway 26 will cause a second gaseous flow into the passageway through the exhaust port 28. This too is illustrated by arrows in FIG. 7.

The first gaseous flow, i.e. the gaseous flow progressing through flow path 38 into passageway 26, intersects with and is in general opposition to the second gaseous flow entering the passageway through exhaust port 28. This will at the very least, substantially reduce the amount of exhaust reversion gases passing into the exhaust pipe. It will be appreciated that the period of negative pressure within passageway 26 is only momentary and the interference between the two gaseous flows will be sufficient to prevent any significant flow of exhaust gases back into the exhaust pipe until arrival of the next positive pressure pulse.

The flow path 38 is, of course, of a generally toroidal configuration and concentrically disposed about exhaust opening 20. The exhaust pipe end portion 18 has a tapered segment 40 wherein the outer peripheral surface 22 gradually reduces in circumference in the direction of the exhaust opening 20. This configuration, coupled with the cone-like configuration of the shroud tends to direct the first gaseous flow passing through flow path 38 toward a point of convergence to ensure that the second gaseous flow entering through the exhaust port 28 is substantially interfered with and impeded.

A baffle 46 is located within the end portion 18 of the exhaust pipe. The baffle 46 is for the purpose of impeding flow in the direction of the internal combustion engine of any portion of the second gaseous flow entering the exhaust opening 20 after intersection thereof with the first gaseous flow, as described above. The baffle is located within the end portion 18 adjacent to the exhaust opening 20.

The baffle 46 includes a plurality of interconnected baffle plates or vanes 48 which, for example, may be constructed of sheet metal such as aluminum and secured together in any desired fashion. The ends of the baffle plates are connected to mounting rings 50, 52 which engage the inner wall of the exhaust pipe, generally conform to the shape thereof, and stabilize the baffle plates in the desired position.

The four baffle plates 48 disclosed in the drawing converge to define a plenum chamber 54 having an interior dminishing in cross-section as the plenum chamber progresses away from exhaust opening 20. The plenum chamber is essentially of pyramidal configuration, closed at the end thereof disposed away from exhaust opening 20 and open at the end closest to the exhaust opening 20. The baffle is so constructed as to allow for the free flow of exhaust gases from the exhaust pipe while interfering with any reversion gases.

FIGS. 6 and 6A provide a schematic illustration of the gas flows relative to the baffle when exhaust is occurring. The exhaust gases caused by the internal combustion engine flow away from the engine through the exhaust pipe (including headers) to the vicinity of the baffle 46. The exhaust gases will be directed by baffle plates 48 along the outside thereof in a space 56 between the baffle plates and the exhaust pipe end portion. The flow will be relatively unimpeded. While there will be pressure built up within space 56, such pressure will not be excessive. In any event, the baffle plates 48 each define a plurality of apertures 60 which will relieve such pressure by venting a portion of the exhaust gases into the interior of the plenum chamber 54 and out the open end thereof in the direction of exhaust opening 20. The baffle plates 48 will impart a swirl or helical twisting to the exhaust gases passing within the space 56.

Referring now to FIGS. 7 and 7A, the flow pattern of any reversionary gases which may get beyond the shroud passageway is shown schematically by arrows. It will be appreciated that gases approaching the baffle 46 from the direction of exhaust opening 20 will, in large measure, enter the plenum chamber 54 through the large opening defined at the pyramidal base thereof.

Bosses 64 surround the apertures 60 and extend into the interior of the plenum chamber. It will be appreciated that these bosses will interfere with the flow path of gases entering the plenum chamber from the direction of the exhaust opening 20. When a positive pressure exists within the plenum chamber, the gases will, of course, be vented through apertures 60 but the flow therethrough will be impeded by the bosses and not smooth. Thus, the baffle plates function in the nature of a trap for most of the reversion gases which may possibly enter the exhaust pipe through the exhaust opening 20.

Additional resistance to reversionary gas flow results from the afore-mentioned swirling of gases during the exhaust phase. Reversionary gases entering space 56 between the baffle plates and the end portion 18 will encounter the remnants of such helical flow and be effectively prevented from progressing beyond the baffle.

In the arrangement illustrated, the baffle 46 is disposed within a conventional "glass pack"-type muffler arrangement comprising a foraminous screen 70 and fiberglass material 72 sandwiched between the screen and the end portion 18. However, it will be appreciated that these conventional components form no part of the present invention and that the present invention may be utilized with or without them.

I claim:

1. Apparatus for use with an internal combustion engine for reducing exhaust back flow during operation of said internal combustion engine, said apparatus comprising, in combination:

an exhaust pipe leading from said internal combustion engine and including an end portion, said end portion having a segment defining an exhaust opening, said segment being tapered and continuously converging in the direction of said exhaust opening and having an outer tapered peripheral surface leading to and terminating at said exhaust opening; and shroud means having a truncated cone-like configuration positioned adjacent to said tapered end portion segment and defining a continuously converging passageway leading from said exhaust opening to an exhaust port formed by said shroud means, said shroud means having an inlet opening and said shroud means and the outer peripheral surface of said end portion tapered segment defining a restricted flow path leading from the inlet opening and providing communication between the ambient atmosphere and said passageway, said exhaust opening being positioned between said inlet opening and said exhaust port, and said end portion segment and said shroud being so configured as to be co-operable upon creation of negative gas pressure in said passageway caused by a negative pressure within said exhaust pipe to induce a first gaseous flow through said flow path and into said passageway intersecting with and in general opposition to a second gaseous flow through said exhaust port resulting from said negative gas pressure in said passageway, said shroud means inlet opening being larger than said exhaust port and said shroud means having a tapered peripheral wall leading from said inlet opening to said exhaust port, said end portion segment exhaust opening being disposed within the confines of said tapered peripheral wall.

2. The apparatus according to claim 1 wherein said shroud means exhaust port is smaller than the end portion exhaust opening.

3. The apparatus according to claim 1 additionally comprising baffle means located within said end portion adjacent to said exhaust opening, said baffle means impeding flow in the direction of said internal combustion engine of any portion of said second gaseous flow entering said exhaust opening after intersection thereof with said first gaseous flow.

4. The apparatus according to claim 3 wherein said baffle means comprises a plurality of interconnected baffle plates within said end portion and converging to define a plenum chamber having an interior diminishing in cross-section as said plenum chamber progresses away from said exhaust opening, said plenum chamber receiving at least some of said second gaseous flow portion.

5. The apparatus according to claim 4 wherein said baffle plates define a plurality of apertures providing communication between the said plenum chamber interior and a space exterior of said plenum chamber defined by said baffle plates and said end portion.

6. The apparatus according to claim 5 additionally comprising bosses surrounding said apertures attached to said baffle plates and extending into the interior of said plenum chamber, said bosses interfering with the flow of said second gaseous flow portion.

7. The apparatus according to claim 1 wherein said exhaust pipe end portion includes a tapered segment wherein said outer peripheral surface gradually reduces in circumference in the direction of said exhaust opening.

8. The apparatus according to claim 1 additionally comprising attachment means for attaching said shroud means to said exhaust pipe end portion.

9. The apparatus according to claim 4 wherein said baffle plates are so configured as to induce a generally helical swirl in exhaust gasses flowing away from said internal combustion engine toward said exhaust opening.

* * * * *